United States Patent [19]
Davankov et al.

[11] Patent Number: 6,153,707
[45] Date of Patent: Nov. 28, 2000

[54] METHOD OF PRODUCING MATERIAL FOR PURIFICATION OF PHYSIOLOGICAL LIQUIDS OF ORGANISM

[75] Inventors: Vadim Davankov; Ludmila Pavlova; Maria Tsyurupa, all of Moscow, Russian Federation

[73] Assignee: Renal Tech International LLC, New York, N.Y.

[21] Appl. No.: 09/210,675

[22] Filed: Dec. 14, 1998

Related U.S. Application Data

[63] Continuation-in-part of application No. 09/019,583, Feb. 6, 1998.

[51] Int. Cl.[7] .............................. C08F 19/12; C08F 8/28; B01L 20/26; B01L 20/00
[52] U.S. Cl. ...................... 525/333.2; 525/385; 502/402; 502/403
[58] Field of Search ................................ 525/385, 333.2; 502/402, 403

[56] References Cited

U.S. PATENT DOCUMENTS

| | | | |
|---|---|---|---|
| 4,140,652 | 2/1979 | Korshak et al. | 252/426 |
| 5,151,191 | 9/1992 | Matkovich et al. | 210/646 |
| 5,218,004 | 6/1993 | Meteyer | 521/53 |
| 5,773,384 | 6/1998 | Meteyer | 502/402 |
| 5,904,663 | 5/1999 | Braverman et al. | 604/5 |

Primary Examiner—David Wu
Assistant Examiner—Tanya Zalukaeva
Attorney, Agent, or Firm—I. Zborovsky

[57] ABSTRACT

A method of producing a material for purification of physiological liquids of organism has the steps of providing a polymer which has a size, a shape, and a structure selected so as to remove toxic compounds from the physiological liquids, chemically modifying a surface of the polymer so as to provide hydrophilicity and biocompatibility, and performing the modification in a medium with a content of organic substance which is efficient for preventing endotoxins contamination of the polymer.

5 Claims, No Drawings

METHOD OF PRODUCING MATERIAL FOR PURIFICATION OF PHYSIOLOGICAL LIQUIDS OF ORGANISM

CROSS-REFERENCE TO A RELATED APPLICATION

This application is a continuation-in-part of patent application Ser. No. 09/019,583 Filed on Feb. 6, 1998.

BACKGROUND OF THE INVENTION

The present invention relates to a method of producting materials for purification of physiological liquids of organisms.

It is known to use for purification of physiological liquids of organism such materials which are based on polymers with a surface modified to provide a greater hydrophilicity and biocompatibility. When physiological liquids of organisms are passed through such materials, toxicants are removed from blood, plasma and other physiological liquids. It has been found that during modification of the surface of the polymers for producing such materials, frequently a contamination with endotoxins takes place. Endotoxins is a degradation product of the cell membrane (walls) of bacteria. They are present on all surfaces, in air and in solution, even after sterilization procedure. The adsorbants have a great affinity for endotoxins. The later binds to the interior surface of the beads of the polymer avidly and is not easily removed. It is therefore very important to avoid contamination of the polymers with the bacteria and endotoxins as much as possible.

SUMMARY OF THE INVENTION

Accordingly, it is an object of the present invention to provide a method of producing materials for purification of physiological liquids of organism, which avoids the disadvantages of the prior art.

More particularly, it is an object of the present invention to provide a method of producing materials for purification of physiological liquids of organism, which prevents contamination of the materials which endotoxins.

In keeping with these objects and with others which will become apparent hereinafter, one feature of present invention resides, briefly stated, in a method of producing a material for purification of physiological liquids of organism which includes providing a polymer having a size, shape and structure selected so as to remove toxic compounds from a physiological liquid, modifying a surface of the polymer to impart to the polymer a greater hydrophilicity and a greater biocompatibility, and performing the modification in a medium with a content of an organic substance sufficient for inhibiting of endotoxins.

When the method is performed in accordance with the present invention, a material for purification of physiological liquids of organism produced by the inventive method is not contaminated with endotoxins.

The novel features which are considered as characteristic for the present invention are set forth in particular in the appended claims. The invention itself, however, both as to its construction and its method of operation, together with additional objects and advantages thereof.

DESCRIPTION OF PREFERRED EMBODIMENTS

One of the materials which can be efficiently used for purification of physiological liquids of organism is a porous hydrophobic divinylbenzene copolymer which initially has surface exposed vinyl groups, in which thereafter the vinyl groups are chemically modified so as to form different surface exposed functional groups with a greater hydrophilicity and greater biocompatibility than those of the vinyl groups. This material is disclosed in our patent application Ser. No. 09/019,583 which is incorporated here as a reference.

The divinylbenzene copolymer of this material is produced in the following manner:

A solution of 130 g p-ethylstyrene, 132 g divinylbenzene (a mixture of para and metha-isomers of about 1:1) and 2.62 g benzoyl peroxide in a mixture of 150 ml toluene and 100 ml iso-amyl alcohol is suspended in 4 liters of pure water containing 1% cellulose stabilizer. After 39 min stirring at room temperature, the mixture is heated at 40° C. for 1 hours, 60° C. for 2 hours, 80° C. for 5 hours and 90° C. for 2 hours. After cooling the mixture to room temperature, the beads of the material obtained are filtered and washed with hot water, methanol and water. The polymer is dried in an oven at 80° C. within one day.

In order to impart a greater hydrophilicity and a greater biocompatibility the surface-exposed vinyl groups of the above mentioned copolymer are modified in accordance with a modification procedure. In accordance with the present invention, the modification procedure is performed in a medium with a content of an organic substance which is a efficient for inhibition of bacterial growth and generation of endotoxins. It has been found that the content of the organic substance in the medium has to be at least 20 vol % to prevent contamination of the polymer with endotoxins.

The modification of the copolymers can be performed in accordance with the following three principal directions.

- grafting hydrophilic polymer chains by a radial polymerization of 2-hydroxyethyl methacrylate, N-vinylpyrrolidone, N-vinylcaprolactame, or other water soluble monomers,
- oxidation of the vinyl groups to epoxy groups with the subsequent reaction of the epoxy groups with water, ethylene glycol, amines or 2-amonoethanol molecules, and
- depositing high-molecular-weight hemocompatible polymer, in particular poly(trifluorethyeoxy) phosphazene onto the surface of the polymeric beads.

This was disclosed in detail in our patent application Ser. No. 09/019,583 which is incorporated here by reference.

Several examples of the modification procedure are presented herein below.

EXAMPLE 1

(Aqueous-organic medium)

5.4 g of the water-washed polymer (dry weight 2.1 g), prepared by polymerization of technical grade 50%-divinylbenzene described in Example, were suspended in a mixture of 3 ml ethanol and 2 ml water and supplied with a solution of 0.05 g of ammonium persulfate in 2 ml water, a solution of 0.035 ml tetramethyl ethylenedlamine in 1 ml ethanol and finally with a solution of 0.03 ml N-vinylpyrrolidone in 1 ml ethanol. The mixture was stirred at 37° C. for 4 hours. Using spectrophotometry at 234 nm, 99% of the initial amount of vinylpyrrolidone were found to graft to the polymer in the above aqueous/ethanolic mixture of the appropriate composition of 7:5 (vol/vol). The final polymer was washed with ethanol and dried to constant weight. The dry polymer can be easily wetted with water, what indicates the presence of hydrophilic grafted polymer layer on the surface of the basically hydrophobic material.

EXAMPLE 2

(Organic medium)

68 g of dry polymer obtained by polymerization of technical-grade 50%-divinylbenzene according to the protocol described in the above Example, were suspended in 350 ml ethanol, supplied with a solution of 1.4 g azo-bis-isobutyro nitrile in 60 ml ethanol, and heated to 60° C. At that temperature the mixture was provided with a solution of 1.0 ml N-vinylpyrrolidone in 10 ml ethanol. After shaking the mixture at 60° C. for 3.5 hours, conversion of vinylpyrrolidone was found to reach 99%. The final polymer thus contained 1.5% polyvinylpyrrolidone.

EXAMPLE 3

(organic medium)

To 1.5 g dry polymer of Example 1 suspended in 5 ml methanol at 40° C. were added 0.04 g layroxyl peroxide in 2 ml methanol and 0.01 ml tetramethyl ethylenediamine in 1 ml methanol. The mixture was heated to 50° C. for 1 hr, supplied with 0.01 ml N-vinylpyrrolidone in 1 ml ethanol and heated further to 60° C. for 3 hours. The polymer was washed with methanol and dried.

EXAMPLE 4

(organic medium)

2 g dry polymer of Example 1 suspended in 10 ml dioxane a solution of 0.08 g lauroyl peroxide in 4 ml dioxane was added. The temperature of the mixture was increased to 60° C. within 10 min, before additional 2 ml dioxane which contained 0.02 ml N-vinylpyrrolidone were added. The reaction mixture was stirred for 3 hr at 60° C. and the polymer was filtered and washed with ethanol.

EXAMPLE 5

(organic medium)

2 g of dry polymer described in Example 1 and suspended in 10 ml ethanol were added at 40° C. with 0.08 g lauroyl peroxide in 4 ml ethanol. In 5 minutes 0.02 ml of tetramethyl ethylenediamine in 2 ml ethanol, and, after another 5 minutes, 0.02 ml N-vinylpyrrolidone in 2 ml ethanol were added. After shaking the mixture for 2.5 hours at 40° C., 80% of the initial vinylpyrrodone were found to be grafted to the polymer surface.

The medium which is used for modification of the polymers can be purely organic; however, it can be for example aqueous-organic and contain at least 20 vol. % of the organic substance.

It has been found that when modification procedure is performed in non-organic, for example purely aqueous medium, the polymer is contaminated with endotoxins, and animals whose blood was purified through the thusly produced material developed fever, which can be considered as indirect indication of the presence of endotoxins in the polymer. In contrast, numerous experiment conducted for purification of physiological liquids of organism with the use of materials modified with the utilization of the medium in accordance with the present invention showed that the polymers were not contaminated with endotoxins.

It is to be understood that other polymers which are used for purification of physiological liquids are modified in the same way in accordance with the present invention,for example polymers disclosed in our patent application Ser. No. 09/019,584 which is incorporated here by reference, as well as other polymers.

It will be understood that each of the elements described above, or two or more together, may also find a useful application in other types of methods differing from the types described above.

While the invention has been illustrated and described as embodied in method of producing material for purification of physiological liquids of organism, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of producing a material for purification of physiological fluids of organism, comprising steps of providing a porous hydrophobic divinylbenzene copolymer with surface exposed vinyl group, which has a size, a shape, and a structure providing removal of toxic compounds from physiological liquids, chemically modifying the surface exposed vinyl groups so as to form different surface exposed groups which are hydrophilic and biocompatible; and performing chemical modification of the surface exposed vinyl groups in a medium with a content of an organic substance which is efficient for preventing endotoxins contamination of the polymer wherein the modification of the copolymers is performed by a method selected from the group consisting of (A) grafting hydrophobic polymer chains by a radical polymerization of 2-hydroxyethyl methacrylate, N-vinylpyrrolidone or N-vinylcaprolactam (B) oxidation of the vinyl groups to epoxy groups with subsequent reaction of the epoxy groups with water, ethylene glycol, amines or 2-aminoethanol and (C) depositing high-molecular weight hermicompatible poly(trifluoroethyloxy)phosphazene onto the surface of the polymeric beads.

2. A method as defined in claim 1, wherein said modifying includes a modifying with the use of the medium which contains at least 20 vol. % of the organic substance.

3. A method as defined in claim 1, wherein said modifying includes a modifying with the use of the medium which is purely organic.

4. A method as defined in claim 1, wherein said modifying includes a modifying with the use of the medium which is aqueous-organic.

5. A method as defined in claim 1, wherein said modifying includes modifying with the use of the medium selected from the group consisting of ethanol, methanol and dioxane.

* * * * *